(12) United States Patent
Nozaki et al.

(10) Patent No.: US 7,977,493 B2
(45) Date of Patent: Jul. 12, 2011

(54) CHEMILUMINESCENT REAGENTS

(75) Inventors: Osamu Nozaki, Osakasayama (JP);
Motonori Munesue, Matsubara (JP);
Hiroko Kawamoto, Yonago (JP)

(73) Assignees: Osamu Nozaki, Osakasayama-shi (JP);
Motonori Munesue, Matsubara-shi (JP);
Hiroko Kawamoto, Yonago-shi (JP);
Chemco Scientific Co., Ltd.,
Takatsuki-shi (JP)

( * ) Notice: Subject to any disclaimer, the term of this patent is extended or adjusted under 35 U.S.C. 154(b) by 356 days.

(21) Appl. No.: 11/494,991

(22) Filed: Jul. 28, 2006

(65) Prior Publication Data
US 2008/0027222 A1    Jan. 31, 2008

(51) Int. Cl.
*C07D 233/70* (2006.01)

(52) U.S. Cl. .................................... 548/316.4

(58) Field of Classification Search ............... 548/316.4
See application file for complete search history.

(56) References Cited

U.S. PATENT DOCUMENTS 4,598,044 A    7/1986  Kricka et al.
4,645,646 A *  2/1987  Gadow et al. .................. 422/61
4,835,101 A *  5/1989  Kao et al. ........................ 435/28
5,106,732 A    4/1992  Kondo et al.
6,565,894 B1 * 5/2003  Smith et al. .................. 424/616

FOREIGN PATENT DOCUMENTS

| JP | 59 171839 A2 | 9/1984 |
|---|---|---|
| JP | 02-174694 | 7/1990 |
| JP | 02-291299 | 12/1990 |
| JP | 03-035147 | 2/1991 |
| JP | 07-327694 | 12/1995 |
| JP | 08-313443 | 11/1996 |

OTHER PUBLICATIONS

Hadd et al. "Stopped-Flow Kinetics Investigation of the Imidazole-Catalyzed Peroxyoxalate Chemiluminescenece Reaction" J. Org. Chem. 1998, vol. 63, pp. 3023-3031.*

* cited by examiner

*Primary Examiner* — Joseph R Kosack
(74) *Attorney, Agent, or Firm* — Flynn, Thiel, Boutell & Tanis, P.C.

(57) ABSTRACT

Chemiluminescent substances are prepared by freezing or lyophilizing a solution of a peroxidized nitrogen-containing five-membered cyclic compound.
The chemiluminescent substances have a sensitivity comparable to that of luminol chemiluminescence, are highly water-soluble, have no incorporation of impurities, are not degraded during storage, have high reproducibility in measurement results, and are very suitable for use in the detection and quantification of various substances in many applications, e.g., clinical applications.

6 Claims, No Drawings

CHEMILUMINESCENT REAGENTS

BACKGROUND OF THE INVENTION

1. Field of the Invention

The present invention relates to novel chemiluminescent reagents for use in the detection and quantification of various substances, for example, in clinical applications.

2. Description of the Related Art

Many clinical methods have been developed to label substances with enzymes and measure the activity of the labeled enzymes by chemiluminescence. Such chemiluminescence measurements are suitable for clinical tests in terms of their simple availability, promptness and high sensitivity. Enzymes used for the chemiluminescence measurements are peroxidases, alkaline phosphotases, glycol oxidases, and the like. Suitable chemiluminescent substances used for the chemiluminescence measurements are luminol, isoluminol, lophine, lucigenin, peryoxalate, and the like. See, the following Patent Publication Nos. 1 to 6.

(Patent Publication No. 1) Japanese Patent Application Laid-Open No. Sho 59-171839
(Patent Publication No. 2) Japanese Patent Application Laid-Open No. Hei 2-174694
(Patent Publication No. 3) Japanese Patent Application Laid-Open No. Hei 2-291299
(Patent Publication No. 4) Japanese Patent Application Laid-Open No. Hei 3-35147
(Patent Publication No. 5) Japanese Patent Application Laid-Open No. Hei 7-327694
(Patent Publication No. 6) Japanese Patent Application Laid-Open No. Hei 8-313443

However, these chemiluminescent substances have the disadvantages of relatively poor solubility in water, which is essential for chemiluminescent detection, incorporation of impurities, and possible degradation during storage.

Specifically, luminol and peryoxalate are required to be dissolved in organic solvents, such as acetonitrile, for the preparation of high-concentration solutions. Lucigenin has the problems of short luminescence retention and severe background noise. Lophine chemiluminescence has the problems of poor water solubility and low luminescence yield.

SUMMARY OF THE INVENTION

Therefore, the present invention has been made in view of the above problems of the conventional chemiluminescent substances used for chemiluminescence measurements, and it is an object of the present invention to provide novel chemiluminescent substances that have a sensitivity comparable to that of luminol chemiluminescence, are highly water-soluble, have no incorporation of impurities, are not degraded during storage, have high reproducibility in measurement results, and are very suitable for use in the detection and quantification of various substances in many applications, e.g., clinical applications.

In accordance with one aspect of the present invention, there is provided a chemiluminescent reagent which is prepared by freezing a solution of a peroxidized nitrogen-containing five-membered cyclic compound.

In accordance with another aspect of the present invention, there is provided a chemiluminescent reagent which is prepared by lyophilizing a solution of a peroxidized nitrogen-containing five-membered cyclic compound.

In preferred embodiments of the present invention, the nitrogen-containing five-membered cyclic compound is selected from pyrrole, imidazole, and purine compounds.

DESCRIPTION OF THE PREFERRED EMBODIMENTS

The chemiluminescent reagents of the present invention will now be described in detail.

The chemiluminescent reagents of the present invention are prepared by freezing or lyophilizing a solution of a peroxidized nitrogen-containing five-membered cyclic compound. Specifically, the chemiluminescent reagents of the present invention are prepared by reacting a solution a nitrogen-containing five-membered cyclic compound, an aqueous hydrogen peroxide solution and an alkaline buffer, and freezing or lyophilizing the reaction solution.

More specifically, the chemiluminescent reagents of the present invention are prepared by introducing a solution of a nitrogen-containing five-membered cyclic compound, an aqueous hydrogen peroxide solution and an alkaline buffer into a test tube, reacting the mixture under heating to about 40° C. to about 60° C. for about 30 minutes, and directly freezing or lyophilizing the test tube.

Storage stability of the chemiluminescent reagents of the present invention could be achieved by simply freezing or lyophilization of the reaction solution or a fraction obtained by high-performance liquid chromatography of the reaction solution. The frozen chemiluminescent reagent of the present invention is allowed to thaw at room temperature and is then used for the detection and quantification of various substances. Alternatively, the lyophilized chemiluminescent reagent of the present invention is dissolved in distilled water in the same volume removed by the lyophilization, and is then used for the detection and quantification of various substances.

The nitrogen-containing five-membered cyclic compound used to prepare the chemiluminescent reagents according to the present invention is selected from pyrrole, imidazole, and purine compounds. Examples of suitable pyrrole compounds include, but are not limited to, pyrrole, proline, and porphyrin. Examples of suitable imidazole compounds include, but are not limited to, imidazole, 2-methylimidazole, 4-methylimidazole, 4-methyl-5-hydroxymethylimidazole, benzimidazole, 4-nitroimidazole, alantoin, ethylene urea, histidine, and pyrazole. Examples of suitable purine compounds include, but are not limited to, theophylline, caffeine, xanthine, allopurinol, inosine, tryptophan, adenine, adenosine, nicotine amide adenine dinucleotide (NAD), reduced nicotine amide adenine dinucleotide (NADH), adenosine triphosphate (ATP), adenosine diphosphate (ADP), adenosine monophosphate (AMP), cyclic AMP, serotonin, and aciclovir.

Non-limiting examples of suitable alkaline buffers that can be used to prepare the chemiluminescent reagents of the present invention include Tricine buffers, Tris hydrochloride buffers, and borate buffers. The concentration of the alkaline buffer used is dependent on the kind of the buffer. A Tricine buffer (pH 9.4) having a concentration of 50 mmol/L is used in the present invention.

The aqueous hydrogen peroxide solution used to prepare the chemiluminescent reagents of the present invention preferably has a concentration of about 100 mmol/L.

EXAMPLES

In the following examples, various chemiluminescent reagents of the present invention were prepared and used to measure the activity of peroxidases.

Example 1

2 mL of a 0.1 mol/L pyrrole solution (pH adjustment with a 50 mmol/L Scene buffer) was introduced into a test tube, and then 0.2 mL of an aqueous hydrogen peroxide (100 mmol) solution was added thereto. The mixture was allowed to react at about 60° C. for about 30 minutes. Thereafter, the test tube was placed and frozen in a freezer, giving a chemiluminescent reagent of the present invention.

After the test tube containing the chemiluminescent reagent thus prepared was taken out of the freezer, the chemiluminescent reagent was thawed at room temperature to obtain a solution. 50 μl of the solution was injected into a flow cell filled with an immobilized peroxidase enzyme using a flow injection system. As a result, it could be confirmed that the chemiluminescent reagent showed a chemiluminescence intensity comparable to that of luminol chemiluminescence.

Example 2

2 mL of a 0.1 mol/L proline solution (pH adjustment with a 50 mmol/L Tricine buffer) was introduced into a test tube, and then 0.2 mL of an aqueous hydrogen peroxide (100 mmol) solution was added thereto. The mixture was allowed to react at about 60° C. for about 30 minutes. Thereafter, the test tube was placed and frozen in a freezer, giving a chemiluminescent reagent of the present invention.

After the test tube containing the chemiluminescent reagent thus prepared was taken out of the freezer, the chemiluminescent reagent was thawed at room temperature to obtain a solution. 50 μl of the solution was injected into a flow cell filled with an immobilized peroxidase enzyme using a flow injection system. As a result, it could be confirmed that the chemiluminescent reagent showed a chemiluminescence intensity comparable to that of luminol chemiluminescence.

Example 3

2 mL of a 0.1 mol/L imidazole solution (pH adjustment with a 50 mmol/L Tricine buffer) was introduced into a test tube, and then 0.2 mL of an aqueous hydrogen peroxide (100 mmol) solution was added thereto. The mixture was allowed to react at about 60° C. for about 30 minutes. Thereafter, the test tube was placed and frozen in a freezer, giving a chemiluminescent reagent of the present invention.

After the test tube containing the chemiluminescent reagent thus prepared was taken out of the freezer, the chemiluminescent reagent was thawed at room temperature to obtain a solution. 50 μl of the solution was injected into a flow all filled with an immobilized peroxidase enzyme using a flow injection system. As a result, it could be confirmed that the chemiluminescent reagent showed a chemiluminescence intensity comparable to that of luminol chemiluminescence.

Examples 4 to 12

2 mL of each of a 2-methylimidazole solution (Example 4), a 4-methylimidazole solution (Example 5), a 4-methyl-5-hydroxymethylimidazole solution (Example 6), a benzimidazole solution (Example 7), a 4-nitroimidazole solution (Example 8), an alantoin solution (Example 9), an ethylene urea solution (Example 10), a histidine solution (Example 11), and a pyrazole solution (Example 12) (all of which had a concentration of 0.1 mol/L and were pH-adjusted with a 50 mmol/L Tricine buffer) was introduced into a test tube, and then 0.2 mL of an aqueous hydrogen peroxide (100 mmol) solution was added thereto. Each mixture was allowed to react at about 60° C. for about 30 minutes. Thereafter, the test tubes were placed and frozen in a freezer, giving chemiluminescent reagents of the present invention.

After the test tube containing each chemiluminescent reagent thus prepared was taken out of the freezer, the chemiluminescent reagent was thawed at room temperature to obtain a solution. 50 μl of the solution was injected into a flow cell filled with an immobilized peroxidase enzyme using a flow injection system. As a result, it could be confirmed that all the chemiluminescent reagents showed a chemiluminescence intensity comparable to that of luminol chemiluminescence.

Example 13

2 mL of a 0.1 mol/L theophylline solution (pH adjustment with a 50 mmol/L Tricine buffer) was introduced into a test tube, and then 0.2 mL of an aqueous hydrogen peroxide (100 mmol) solution was added thereto. The mixture was allowed to react at about 60° C. for about 30 minutes. Thereafter, the test tube was placed and frozen in a freezer, giving a chemiluminescent reagent of the present invention.

After the test tube containing the chemiluminescent reagent thus prepared was taken out of the freezer, the chemiluminescent reagent was thawed at room temperature to obtain a solution. 50 μl of the solution was injected into a flow cell filled with an immobilized peroxidase enzyme using a flow infection system. As a result, it could be confirmed that the chemiluminescent reagent showed a chemiluminescence intensity comparable to that of luminol chemiluminescence.

Examples 14 to 26

2 mL of each of a caffeine solution (Example 14), a xanthine solution (Example 15), an allopurinol solution (Example 16), an inosine solution (Example 17), a tryptophan solution (Example 18), an adenine solution (Example 19), an adenosine solution (Example 20), an NAD solution (Example 21), an NADH solution (Example 22), an ATP solution (Example 23), an ADP solution (Example 24), an AMP solution (Example 25), and a cyclic AMP solution (Example 26) (all of which had a concentration of 0.1 mol/L and were pH-adjusted with a 50 mmol/L Tricine buffer) was introduced into a test tube, and then 0.2 mL of an aqueous hydrogen peroxide (100 mmol) solution was added thereto. Each mixture was allowed to react at about 60° C. for about 30 minutes. Thereafter, the test tubes were placed and frozen in a freezer, giving chemiluminescent reagents of the present invention.

After the test tube containing each chemiluminescent reagent thus prepared was taken out of the freezer, the chemiluminescent reagent was thawed at room temperature to obtain a solution. 50 μl of the solution was injected into a flow cell filled with an immobilized peroxidase enzyme using a flow injection system. As a result, it could be confirmed that all the chemiluminescent reagents showed a chemiluminescence intensity comparable to that of luminol chemiluminescence.

Example 27

2 mL of a 0.1 mol/L pyrrole solution (pH adjustment with a 50 mmol/L Tricine buffer) was introduced into a test tube, and then 0.2 mL of an aqueous hydrogen peroxide (100 mmol) solution was added thereto. The mixture was allowed to react at about 60° C. for about 30 minutes. Thereafter, the test tube was placed and lyophilized in a freeze-dryer, giving a chemiluminescent reagent of the present invention.

2 mL of distilled water was added to the test tube to dissolve the chemiluminescent reagent. 50 μl of the solution was injected into a flow cell filled with an immobilized peroxidase enzyme using a flow injection system. As a result, it could be confirmed that the chemiluminescent reagent showed a chemiluminescence intensity comparable to that of luminol chemiluminescence.

Example 28

2 mL of a 0.1 mol/L proline solution (pH adjustment with a 50 mmol/L Tricine buffer) was introduced into a test tube, and then 0.2 mL of an aqueous hydrogen peroxide (100 mmol) solution was added thereto. The mixture was allowed to react at about 60° C. for about 30 minutes. Thereafter, the test tube was placed and lyophilized in a breeze-dryer, giving a chemiluminescent reagent of the present invention.

2 mL of distilled water was added to the test tube to dissolve the chemiluminescent reagent. 50 μl of the solution was injected into a flow cell filled with an immobilized peroxidase enzyme using a flaw injection system. As a result, it could be confirmed that the chemiluminescent reagent showed a chemiluminescence intensity comparable to that of luminol chemiluminescence.

Example 29

2 mL of a 0.1 mol/L imidazole solution (pH adjustment with a 50 mmol/L Tricine buffer) was introduced into a test tube, and then 0.2 mL of an aqueous hydrogen peroxide (100 mol) solution was added thereto. The mixture was allowed to react at about 60° C. for about 30 minutes. Thereafter, the test tube was placed and lyophilized in a freeze-dryer, giving a chemiluminescent reagent of the present invention.

2 mL of distilled water was added to the test tube to dissolve the chemiluminescent reagent. 50 μl of the solution was injected into a flow cell filled with an immobilized peroxidase enzyme using a flow injection system. As a result, it could be confirmed that the chemiluminescent reagent showed a chemiluminescence intensity comparable to that of luminol chemiluminescence.

Examples 30 to 38

2 mL of each of a 2-methylimidazole solution (Example 30), a 4-methylimidazole solution (Example 31), a 4-methyl-5-hydroxymethylimidazole solution (Example 32), a benzimidazole solution (Example 33), a 4-nitroimidazole solution (Example 34), an alantoin solution (Example 35), an ethylene urea solution (Example 36), a histidine solution (Example 37), and a pyrazole solution (Example 38) (all of which had a concentration of 0.1 mol/L and were pH-adjusted with a 50 mmol/L Tricine buffer) was introduced into a test tube, and then 0.2 mL of an aqueous hydrogen peroxide (100 mmol) solution was added thereto. Each mixture was allowed to react at about 60° C. for about 30 minutes. Thereafter, the test tubes were placed and lyophilized in a freeze-dryer, giving chemiluminescent reagents of the present invention.

2 mL of distilled water was added to the test tube containing each chemiluminescent reagent thus prepared to dissolve the chemiluminescent reagent. 50 μl of the solution was injected into a flow cell filled with an immobilized peroxidase enzyme using a flow injection system. As a result, it could be confirmed that all the chemiluminescent reagents showed a chemiluminescence intensity comparable to that of luminol chemiluminescence.

Example 39

2 mL of a 0.1 mol/L theophylline solution (pH adjustment with a 50 mmol/L Tricine buffer) was introduced into a test tube, and then 0.2 mL of an aqueous hydrogen peroxide (100 mmol) solution was added thereto. The mixture was allowed to react at about 60° C. for about 30 minutes. Thereafter, the test tube was placed and lyophilized in a freeze-dryer, giving a chemiluminescent reagent of the present invention.

2 mL of distilled water was added to the test tube to dissolve the chemiluminescent reagent. 50 μl of the solution was injected into a flow cell filled with an immobilized peroxidase enzyme using a flow injection system. As a result, it could be confirmed that the chemiluminescent reagent showed a chemiluminescence intensity comparable to that of luminol chemiluminescence.

Examples 40 to 52

2 mL of each of a caffeine solution (Example 40), a xanthine solution (Example 41), an allopurinol solution (Example 42), an inosine solution (Example 43), a tryptophan solution (Example 44), an adenine solution (Example 45), an adenosine solution (Example 46), an NAD solution (Example 47), an NADH solution (Example 48), an ATP solution (Example 49), an ADP solution (Example 50), an AMP solution (Example 51), and a cyclic AMP solution (Example 52) (all of which had a concentration of 0.1 mol/L and were pH-adjusted with a 50 mmol/L Tricine buffer) was introduced into a test tube, and then 0.2 mL of an aqueous hydrogen peroxide (100 mmol) solution was added thereto. Each mixture was allowed to react at about 60° C. for about 30 minutes. Thereafter, the test tubes were placed and lyophilized in a freeze-dryer, giving chemiluminescent reagents of the present invention.

2 mL of distilled water was added to the test tube containing each chemiluminescent reagent thus prepared to dissolve the chemiluminescent reagent. 50 μl of the solution was injected into a flow cell filled with an immobilized peroxidase enzyme using a flow injection system. As a result, it could be confirmed that all the chemiluminescent reagents showed a chemiluminescence intensity comparable to that of luminol chemiluminescence.

As apparent from the above description, the chemiluminescent substances of the present invention have a sensitivity comparable to that of luminol chemiluminescence, are highly water soluble, have no incorporation of impurities, are not degraded during storage, emit light by direct oxidation, have high reproducibility in measurement results, and are very suitable for use in the detection and quantification of various substances in many applications, e.g., clinical applications.

What is claimed is:

1. In a chemiluminescent reagent which detects a target substance by the emission of light, the improvement comprising the chemiluminescent reagent being prepared by freezing an aqueous solution consisting of a peroxidized imidazole chemiluminescence material and a tricine buffer, wherein the aqueous solution is produced by mixing an aqueous hydrogen peroxide solution, an imidazole solution and a tricine buffer.

2. The chemiluminescent reagent of claim 1, wherein the tricine buffer has a concentration of 50 mmol/L.

3. The chemiluminescent reagent of claim 1, wherein the aqueous hydrogen peroxide solution has a concentration of about 100 mmol/L and the imidazole solution has a concentration of 0.1 mol/L.

4. In a chemiluminescent reagent which detects a target substance by the emission of light, the improvement comprising the chemiluminescent reagent being prepared by lyophilizing an aqueous solution consisting of a peroxidized imidazole chemiluminescence material and a tricine buffer, wherein the aqueous solution is produced by mixing an aqueous hydrogen peroxide solution, an imidazole solution and a tricine buffer.

5. The chemiluminescent reagent of claim 4, wherein the tricine buffer has a concentration of 50 mmol/L.

6. The chemiluminescent reagent of claim 4, wherein the aqueous hydrogen peroxide solution has a concentration of about 100 mmol/L and the imidazole solution has a concentration of 0.1 mol/L.

* * * * *